United States Patent
Leiden et al.

(12) 
(10) Patent No.: US 6,316,419 B1
(45) Date of Patent: *Nov. 13, 2001

(54) INDUCTION OF ANGIOGENESIS IN HEART MUSCLE BY A DNA SEQUENCE ENCODING AN ANGIOGENIC PROTEIN

(75) Inventors: Jeffrey M. Leiden; Eliav Barr, both of Ann Arbor, MI (US)

(73) Assignee: University of Michigan, Ann Arbor, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/909,496

(22) Filed: Aug. 12, 1997

Related U.S. Application Data (63) Continuation of application No. 08/376,521, filed on Jan. 23, 1995, now Pat. No. 5,661,133, which is a continuation of application No. 07/789,983, filed on Nov. 12, 1991, now abandoned.

(51) Int. Cl.⁷ .............................. A01N 43/04; A61K 31/70
(52) U.S. Cl. ........................... 514/44; 424/93.2; 424/93.6
(58) Field of Search ........................... 514/44; 435/320.1, 435/455; 424/93.2, 93.6

(56) References Cited

U.S. PATENT DOCUMENTS 5,580,859 * 12/1996 Felgner et al. ........................ 514/44
5,661,133 * 8/1997 Leiden et al. ........................ 514/44

OTHER PUBLICATIONS

Verma et al (1997) nature 389, 239–242.*
Anderson (Sep. 1995) Scientific American, 124–126 and 128.*
Blau et al (Nov. 2, 1995) New Eng. J. Med., 1204–1207.*
Losordo et al (1998) Circul. 98, 2800–2804.*
Giordano et al (1996) Nature Medicine 2, 534–539.*
Gramolini et al (1997) BioEssays 19, 747–750.*
Johnson et al (1989) Mole. Cell. Biol. 9, 3393–3399.*
Zhan et al. (1988) Molec. Cell. Biol 8, 3487–3495.*

* cited by examiner

*Primary Examiner*—Deborah Crouch
(74) *Attorney, Agent, or Firm*—Brinks Hofer Gilson & Lione (57) ABSTRACT

A novel method for expressing a protein which comprises: transforming skeletal myoblasts or cardiac myocytes with a DNA sequence comprising a DNA segment encoding a selected gene downstream of the Rous sarcoma virus long terminal repeat or the expression sequence in pRSV, and implanting said skeletal myoblasts or cardiac Myocytes into a recipient which then expresses a physiologically effective level of said protein.

16 Claims, 8 Drawing Sheets

| TIME | PLASMID | NUMBER β-gal POSITIVE HEARTS |
|---|---|---|
| 3-5 DAYS | pRSV-βgal | 12/15 |
| | MOCK | 0/8 |
| 3-4 WEEKS | pRSV-βgal | 8/11 |
| | MOCK | 0/4 |
| 6 MONTHS | | 2/3 |

INDUCTION OF ANGIOGENESIS IN HEART MUSCLE BY A DNA SEQUENCE ENCODING AN ANGIOGENIC PROTEIN

This application is a continuation of application Ser. No. 08/376,521, filed Jan. 23, 1995, U.S. Pat. No. 5,661,113 which is a continuation of 07/789,983, filed Nov. 12, 1991, abandoned

BACKGROUND OF THE INVENTION

1. Field of the Invention

The present invention relates to the use of skeletal and muscle cardiac cells that continuously secrete recombinant protein products.

2. Discussion of the Background

A large number of inherited and acquired diseases require treatment by intravenous or subcutaneous infusions of proteins. These include inherited protein deficiencies such as hemophilia A and B, and congenital growth hormone deficiency, as well as acquired diseases such as AIDS and diabetes mellitus. Standard therapy for such diseases requires repeated intravenous or subcutaneous administration of protein solutions. The ability to use cell implants which continuously secrete recombinant protein products into the circulation would greatly simplify the therapy of many of these disorders. This disclosure describes transplantable genetically-engineered skeletal muscle stem cells (myoblasts) that produce detectable levels of serum proteins in a recipient host and myocytes that produce local levels of secreted recombinant proteins in the myocardium.

Somatic gene therapy can be defined as the ability to program the expression of foreign genes in non-germ line (i.e., non-sperm and egg) cells of an animal or patient. Recent advances in molecular biology including the cloning of many human genes and the development of viral and chemical gene delivery systems have brought us to the threshold of somatic gene therapy. All methods of gene therapy can be divided into two categories: ex vivo gene therapy involves the removal of cells from a host organism, introduction of a foreign gene into those cells in the laboratory, and reimplantation or transplantation of the genetically modified cells back into a recipient host.

In contrast, in vivo gene therapy involves the introduction of a foreign gene directly into cells of a recipient host without the need for prior removal of those cells from the organism. There are a number of requirements that must be met by any method of gene therapy before it can be considered potentially useful for human therapeutics. First, one must develop an efficient method for introducing the foreign gene into the appropriate host cell. Secondly, it would be preferable to develop systems that program expression of the gene only in the appropriate host cell type, thus preventing expression of the foreign gene in an inappropriate cell. Finally, and most importantly when considering human gene therapy, the technique must have a minimal risk of mutating the host cells and of causing a persistent infection of the host organism, a particularly important worry when using virus vectors to introduce foreign genes into host cells. This application pertains to novel somatic gene therapy for use in heart and skeletal muscle which meets these requirements.

A. In Vivo Gene Therapy in Cardiac Myocytes

The ability to program recombinant gene expression in cardiac myocytes enables the treatment of a number of inherited and acquired cardiac diseases. Therapeutic applications of this approach can be divided into several general categories. First, to correct genetic disorders of myocardial cells. For example, injection of the normal dystrophin cDNA can be used to correct the defects in cardiac contractility seen in patients with Duchenne's muscular dystrophy. Secondly, to stimulate new collateral circulation in areas of chronically ischemic myocardium by injecting plasmids encoding recombinant angiogenesis factors directly into the left ventricular wall. Also, this approach can be used to directly study the molecular mechanisms regulating cardiac myocyte gene expression both during cardiac myogeneses and in a variety of pathophysiologic states such as cardiac hypertrophy.

As many as 1.5 million patients per year in the U.S. suffer a myocardial infarction (MI). Many millions more suffer from syndromes of chronic myocardial ischemia due to large and small vessel coronary atherosclerosis. Many of these patients will benefit from the ability to stimulate collateral vessel formation in areas of ischemic myocardium. The direct DNA injection method provides an alternative approach to the current methods of coronary artery bypass and percutaneous transluminal coronary angioplasty. In particular, many patients have such severe and diffuse atherosclerosis that they are not candidates for CABG or PTCA. Thus far, there has been no approach which has successfully stimulated collateral vessel formation in areas of ischemic myocardium.

A number of genetic disorders affect myocardial performance. For example, many patients with Duchenne's muscular dystrophy also suffer from a cardiomyopathy. In addition, it is clear that there are a number of other genetically-inherited cardiomyopathies of unknown etiology. The gene injection approach described in this disclosure is useful for treating a variety of these inherited disorders of cardiac function. For example, injection of vectors containing the normal dystrophin gene or cDNA can correct the defect in patients with Duchenne's muscular dystrophy. Some aspects of the natural expression of the dystrophin gene in muscle from DMD patients are discussed by Scott et al, Science, 239:1418 (1988). As additional genes for inherited cardiomyopathy are identified, these gene products might also be injected into hearts in order to correct abnormal cardiac function.

An understanding of the molecular mechanisms that regulate cardiac-specific gene expression during both normal cardiac development and a variety of pathological processes such as cardiac hypertrophy is critical in designing rational therapeutic approaches to such problems. Previous approaches have all utilized in vitro transfection protocols into neonatal cardiocytes or transgenic approaches in mice. Such studies are complicated by the fact that neonatal cardiocytes may not reflect the in vivo situation and by the fact that neonatal cardiocytes have an extremely limited life span in tissue culture and cannot be incorporated into the heart. Moreover, transgenic approaches are lengthy (requiring 6 months to 1 year) technically difficult and expensive. The gene injection approach described in this disclosure obviates these problems because it allows the stable expression of recombinant gene products in both neonatal and adult cardiac myocytes in vivo in as little as 5 days following injection of DNA.

B. Ex Vivo Gene Therapy Using Skeletal Myoblasts

A variety of acquired and inherited diseases are currently treated by repeated intravenous or subcutaneous infusions of recombinant or purified proteins. These include diabetes mellitus, treated with subcutaneous or intravenous injections of insulin, hemophilia A, treated with intravenous infusions of factor VIII, and pituitary dwarfism, treated with subcutaneous injections of growth hormone. The development of cellular transplantation systems that can stably produce and deliver such recombinant proteins into the systemic circulation would represent an important advance in our ability to treat such diseases. The ideal recombinant protein delivery system would utilize a cell that can be easily isolated from the recipient, grown and transduced with recombinant genes in vitro, and conveniently reimplanted into the host organism. This cell would produce large amounts of secreted recombinant protein, and following secretion, this protein would gain access to the circulation. Finally, such implanted, genetically engineered cells should survive for long periods of time and continue to secrete the transduced protein product without themselves interfering with the function of the tissue into which they were implanted.

Several different cellular systems have been used to produce recombinant proteins in vivo. These include karatinoxytes (M. Flowers et al, PNAS (USA) 87, 2349 (1990)), skin fibroblasts (T. D. Palmer, A. R. Thompson, A. D. Miller, Blood 73, 438 (1989); R. Scharfmann, J. H. Axelrod, I. M. Verma, PNAS (USA) 88, 4626 (1991)), hepatocytes (D. Armentary, A. Thompson, G. Darlington, S. Woo, PNAS (USA) 87, 6141 (1990); K. P. Ponder et al, PNAS (USA) 88, 1217 (1991)), lymphocytes (K. Culver et al, PNAS (USA) 88, 3155, (1991)), and bone marrow (E. Dzierzak, T. Papayannopoulou, R. Mulligan, PNAS (USA) 87, 439 (1990); M. Kaleko, J. V. Garcia, W. R. A. Osborne, A. D. Miller, Blood 75, 1733 (1990)). Although several of these systems have produced detectable levels of circulating proteins, it has proven difficult to produce stable, physiological levels of circulating recombinant proteins in normal animals.

Burnetti et al, J. Biol. Chem., 265:5960 (1990) have studied the regulation of myogenin and the events that occur when myoblasts transform into myocytes. However, no expression of a recombinant DNA sequence was disclosed. Paulson et al, J. Cell Biol., 110:1705 (1990) describes the temperature-sensitive expression of all-torpedo and torpedo-rat hybrid acetylcholine receiptor (AChR in mammalian muscle cells. However, this expression of protein was performed in mouse fibroblasts in culture, and not in vivo. Obtaining expression of physiological serum levels of a protein through a cellular implant is unrelated to and unsuggested by simply obtaining in vitro expression.

Pramanik et al, Eur. J. Biochem., 172:355 (1988). Showed that translation of P-40 mRNA is repressed in non-proliferating myotubes by using nuclease S1 mapping to quantify the steady-stay levels of P-40 mRNA in subcellular fractions of both myoblasts and myotubes. It was shown that the result of the subcellular distribution of this mRNA in proliferating myoblasts following inhibition of DNA synthesis by citazene or arabinoside have shown that translation of P-40 mRNA continued in the absence of DNA synthesis. This observation suggests that an additional signal is necessary to block the translation of P-40 mRNA in myotubes.

Arnold et al (J. Biol. Chem. 257:9872 (1982)) studied expression of glyceraldehyde-3-phosphate dehydrogenase mRNA in developing chick heart cells in cultures. The gap dehydrogenase mRNA was present in 5 hour old dividing myoblasts. This method is limited to in vitro protein expression and does not address the issue of whether skeletal myoblasts will produce secreted recombinant proteins following differentiation into myotubes.

SUMMARY OF THE INVENTION

Accordingly, one object of the invention is to provide a method for expressing physiological levels of recombinant proteins so as to treat inherited or acquired diseases which comprises: implanting skeletal myoblasts into a patient suffering from said condition, wherein said myoblasts are transformed with a DNA sequence comprising a DNA segment encoding a selected gene downstream of the Rous sarcoma virus long terminal repeat or the expression sequence in pRSV to thereby obtain a physiologically effective level of the gene product of said selected gene in the blood.

Another object of the invention is to directly transduced cardiac myocytes in vivo with a DNA sequence comprising a DNA segment encoding a selected gene downstream of the Rous sarcoma virus long terminal repeat or the expression sequence in pRSV, capable of expressing the gene product of said selected gene in the myocardium of the host organism.

BRIEF DESCRIPTION OF THE DRAWINGS

FIGS. 1(A–C)—Secretion of hGH over time by the G19 clone.

FIGS. 2(A–B)—Expression of hGH in muscle and serum of. C2C12 myoblast-injected mice.

FIGS. 3(A–E)—Photomicrographs of BAG-infected C2C12 cells and muscle from C3H mice injected with BAG-infected C2C12 cells.

FIGS. 5(A–D)—Photomicrographs showing expression of β-galactosidase in heart muscle.

DETAILED DESCRIPTION OF THE PREFERRED EMBODIMENTS

A. Skeletal Myoblasts as a Protein Delivery System

A novel plasmid vector, pRSV Growth Hormone (pRSVGH) was constructed by cloning a commercially available human growth hormone gene into a Rous sarcoma virus pRSV expression vector constructed in my laboratory. Murine C2C12 myoblasts were stably co-transfected with two plasmids: (i) the pRSVGH plasmid containing the human growth hormone gene under the control of the Rous sarcoma virus long terminal repeat (RSV LTR) and (ii) the pRSVneo plasmid which encodes resistance to the antibiotic G418. C2C12 is a continuous cell line that has been shown to differentiate into non-dividing, multinucleated myotubes in vitro. These myotubes express the full complement of myofibrillar proteins and display contractile activity. After exposure to G418 to select for stable transfectants, 2 out of 24 clones were shown to produce and secrete relatively high levels of hGH in vitro (2.5 and 9 ng/hr/$10^6$ cells) and one of these, G19, was expanded for further studies.

Figure 1A:
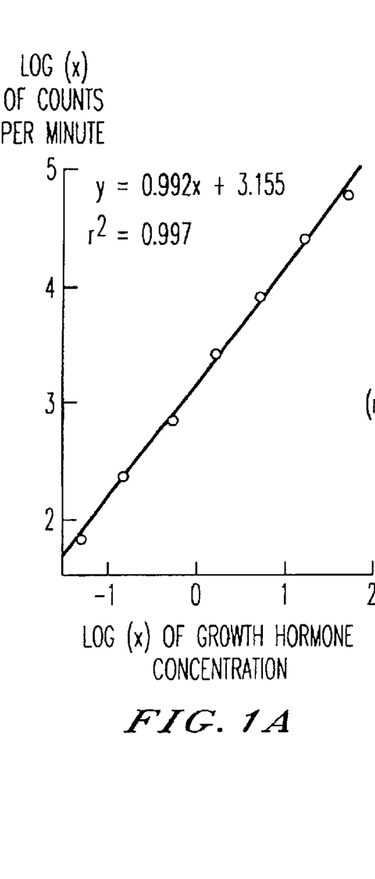
Figure 1B:
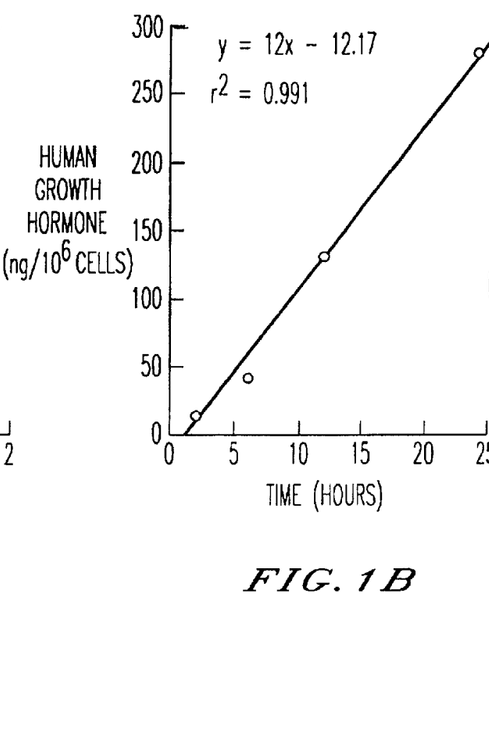
Figure 1C:
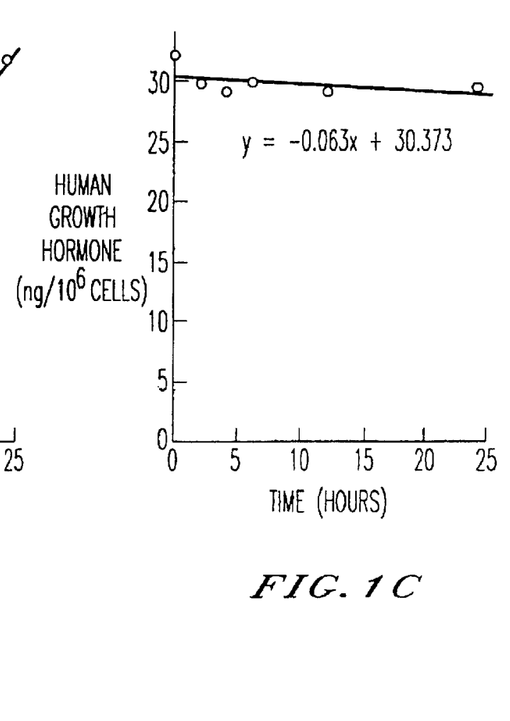
Figure 2A:
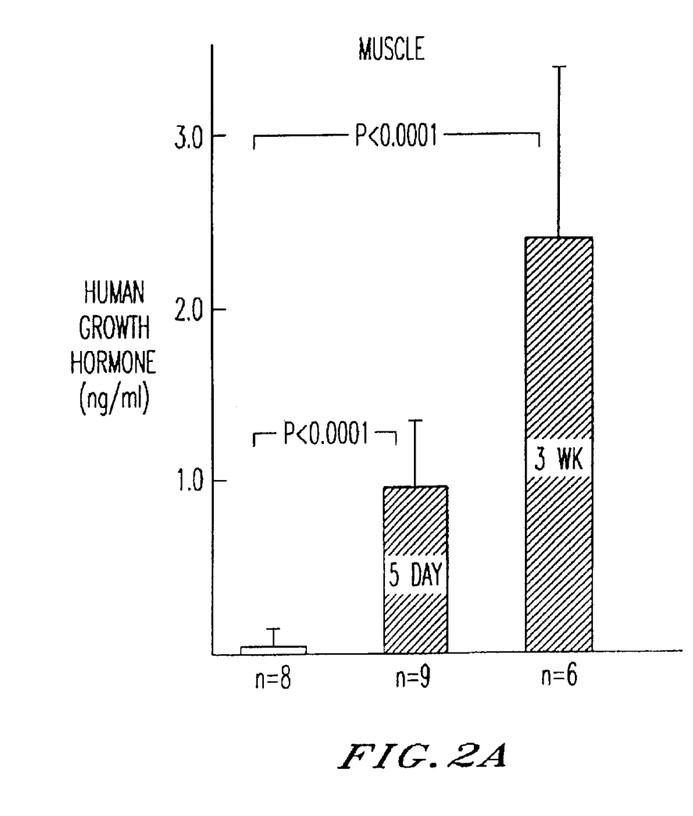
Figure 2B:
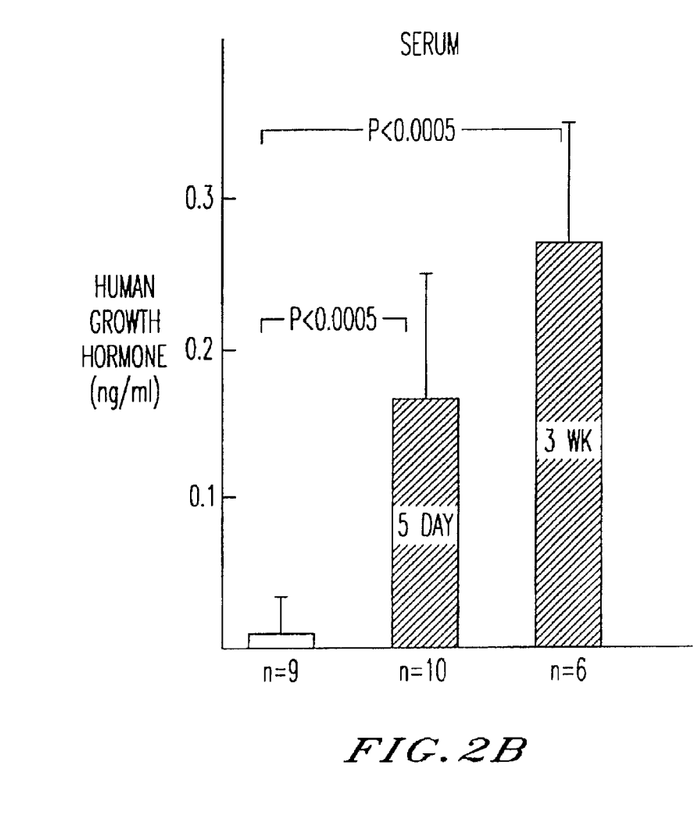

In an initial series of experiments, the in vitro production and secretion of hGH by G19 cells was quantitated using a sensitive radioimmunoassay (RIA). This assay was linear over a range of hGH concentrations between 0.05 and 50 ng/ml (FIG. 1A). Levels of hGH in the culture medium of G19 cells increased in a linear fashion between 2 and 24 hours, with a mean rate of production of 12 ng/hour/$10^6$ cells (FIG. 1B). After secretion, there was almost no degradation of hGH as evidenced by the finding that the levels of hGH from culture supernatants of G19 cells did not decrease significantly after incubation for 24 hours on monolayers of non-transfected C2C12 cells (FIG. 1C). Following differentiation into myotubes in vitro, the hGH-transfected G19 cells continued to secrete hGH at a rate of 6 ng/hr/$10^6$ cells. Thus, non-dividing myotubes retain the ability to produce secreted proteins. Finally, the RIA used in these experiments were specific for hGH and did not cross-react with murine GH (FIG. 2B).

To determine whether G19 cells could produce circulating levels of hGH in vivo, a total of $6 \times 10^6$ G19 cells were injected intramuscularly into 6 separate sites in the lower limbs of normal 4-week-old syngeneic C3H mice. Control mice received identical injections of F17 cells, a G418-resistant clone of C2C12 that does not produce hGH. To prevent potential cellular or antibody-mediated immune responses by the C3H mice to the human growth hormone produced by the G19 cells, all mice received daily injections of cyclosporin A (5 mg/kg, IM). Mice were killed 5 days or 3 weeks after injections, and muscle from the site of injection as well as serum were assayed for hGH (FIG. 2). Muscle lysates from mice injected with the G19 hGH-producing cells contained 1.01±0.34 ng/ml (mean±S.D.) of human growth hormone at 5 days and 2.43±0.97 ng/ml at 3 weeks as compared to control-injected mouse muscle which contained 0.01±0.01 ng/ml (P<0.0001). The serum from G19-injected animals contained 0.16±0.08 ng/ml and 0.28±0.08 ng/ml of hGH at 5 days and 3 weeks following injection, respectively. These values were significantly different from those of control mice (0.01±0.02 ng/ml) (P<0.0005) at both time points. Thus, hGH expression appeared to be stable for at least 3 weeks in these animals.

It was of interest to compare the levels of hGH in the myoblast-injected mice to physiological levels of hGh in human serum. GH is secreted in a pulsatile fashion in humans with normal physiological levels ranging between 0.1 and 25 ng/ml. Absolute levels of hGH also vary depending upon the type of sample tested and the particular assay system used. Serum samples from normal human volunteers (n=7) contained 0.2±01 ng/ml of hGH as compared to 0.28 ng/ml, the mean serum level of hGH in the G19-injected mice. Thus, serum from the G19-injected animals contained physiological levels of hGH 3 weeks after a single injection of $6 \times 10^6$ hGH-transfected myoblasts. Finally, animals were also injected with $6 \times 10^6$ G19 cells without concomitant immunosuppression with cyclosporin A. Serum from these animals (n=4) contained 1.0±0.25 ng/ml of hGH 3 weeks following myoblast injection. Thus, immunosuppression does not appear to be necessary for the short-term production of recombinant proteins following myoblast injection.

Figure 3A:
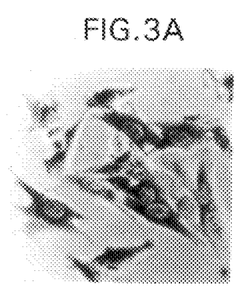
Figure 3B:
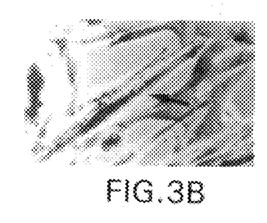
Figure 3C:
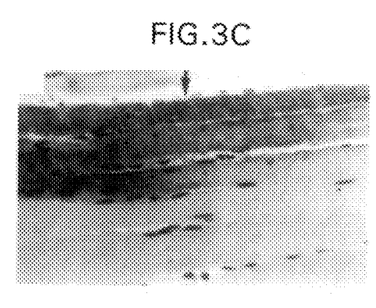
Figure 3D:
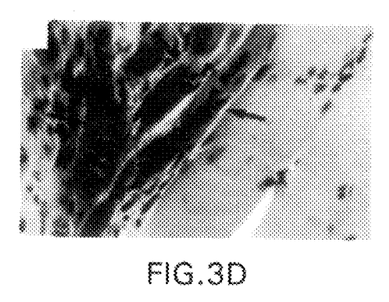
Figure 3E:
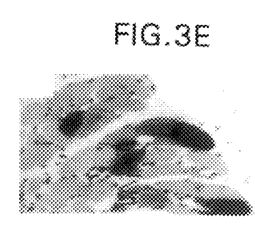

An important question regarding the long-term feasibility of myoblast injections concerns the fate of the myoblasts after IM injection. To address this question, C3H mice were injected with C2C12 myoblasts that had been previously infected in vitro with the β-galactosidase expressing BAG retrovirus and shown to express high levels of intracellular β-galactosidase (FIG. 3A). β-Galactosidase expressing blue C2C12 cells were observed as clusters within areas of normal muscle (FIGS. 3C–E). Whereas the BAG-infected C2C12 myoblasts displayed a mononuclear fibroblast-like appearance when grown in high levels of serum In vitro (FIG. 3A), following injection many of these cells fused into multinucleated myotubes (FIGS. 3C–E) similar to those observed after the differentiation of C2C12 cells by growth in low serum in vitro (FIG. 3B). In no case were tumors detected in the muscle or other organs of the C2C12 myoblast-injected animals at either 5 days or 3 weeks after injection. Moreover, lysates from the non-injected upper limbs, hearts, livers, kidneys, and lungs of the G19-injected animals were devoid of hGH activity demonstrating that the injected cells remained localized to the site of injection. However, because C2C12 is a continuous cell line, an accurate assessment of the malignant potential of the injected G19 cells will require long-term follow-up of these animals. Finally, the p-galactosidase expression seen in vivo was not due to the infection of endogenous muscle with helper virus from the BAG-infected C2C12 cells because no helper virus could be detected by co-cultivation assays using these cells and because retroviruses are unable to infect non-dividing cells such as myotubes. Therefore, these results show that genetically-modified C2C12 cells can become incorporated into the injected muscle by differentiating into multinucleated myotubes in viva.

Genetically engineered myoblasts are a useful delivery system for recombinant proteins in vivo. These cells can produce large amounts of secreted recombinant proteins. They can be stably introduced into muscle by simple IM injection, and their secreted protein products gain access to the circulation. The finding that the technique can be used to produce detectable levels of hGH is especially encouraging given the short half-life of hGH (less than 20 minutes) as compared with those of other serum proteins.

Although all of the studies described above were performed with the immortalized C2C12 cell line, identical techniques are directly applicable to primary human myoblasts. Previous reports have clearly demonstrated that primary human myoblasts can be readily isolated, expanded in vitro, and reinjected into muscle. Like the C2C12 myoblasts, normal myoblasts can become incorporated into the injected muscle by differentiating into multinucleated myotubes in vivo. The unique finding of the present invention is that it is possible to program the expression of a secreted recombinant protein in myoblasts in vitro and that, following injection of these myoblasts into normal animals, they fuse into myotubes and continue to produce the secreted recombinant protein which gains access to the circulation. Thus, analogous techniques to those described could easily be used to transfect primary myoblasts which could then be introduced by intramuscular injection into normal animals or humans.

This same system can express a wide variety of serum proteins such as human factor VIII and factor IX as well as insulin. A number of other cellular implant systems have been tried for the production of serum proteins. These include keratinocytes and hepatocytes. To our knowledge, none of these systems has successfully produced stable and physiological levels of a recombinant protein in normal animals.

B. In Vivo Gene Therapy at Cardiac Myocytes Following Direct Injection of DNA

In another embodiment of the present invention it is possible to program recombinant gene expression in cardiac myocytes after direct injection of DNA into the left ventricular wall. Functional recombinant protein expression in myocytes was demonstrated directly using an enzymatic assay for β-galactosidase. Recombinant gene expression was observed in myocytes from seven of nine of the injected hearts at both 3–5 days and 3–4 weeks after injection. Expression was patchy and was observed only in direct contiguity with the site of injection. These findings have several implications regarding both the use of this method for somatic gene therapy in the heart and the biology of recombinant DNA uptake and expression in muscle cells.

The technique of somatic gene therapy using direct DNA injection into myocardium has several advantages compared with other previously described methods of gene therapy. First, infectious viral vectors are not required, eliminating the possibility of persistent infection of the host. Second, a previous study (Wolff J A, Malone R W, Williams P, Chong W, Acsadi G, Jani A, Felgner P L: Direct gene transfer into mouse muscle in vivo. Science 1990;247:1465–1468) has suggested that recombinant DNA taken up and expressed in skeletal myocytes persists as an episome and therefore does not have the same potential for host cell mutagenesis as do retroviral vectors that integrate into the host chromosome. Finally, this method does not require the growth of recipient cells in vitro, a requirement that would render transfection on nondividing cardiac myocytes particularly difficult.

Direct injection of recombinant DNA into the myocardium is useful for the treatment of many acquired and inherited cardiovascular diseases in particular, by stimulating collateral circulation in areas of chronic myocardial ischemia by expressing recombinant angiogenesis factors locally in the ventricular wall.

We have demonstrated that a recombinant bacterial β-galactosidase gene under the control of the Rous sarcoma virus promoter can be introduced into and expressed in adult rat cardiac myocytes in vivo by the injection of purified plasmid DNA directly into the left ventricular wall. Cardiac myocytes expressing the recombinant β-galactosidase activity have been detected histochemically in rat hearts for at least six months following injection of the recombinant β-galactosidase gene. Rats have now been injected with the β-galactosidase gene for studies of the stability of expression at one year post-injection.

Figure 4A:
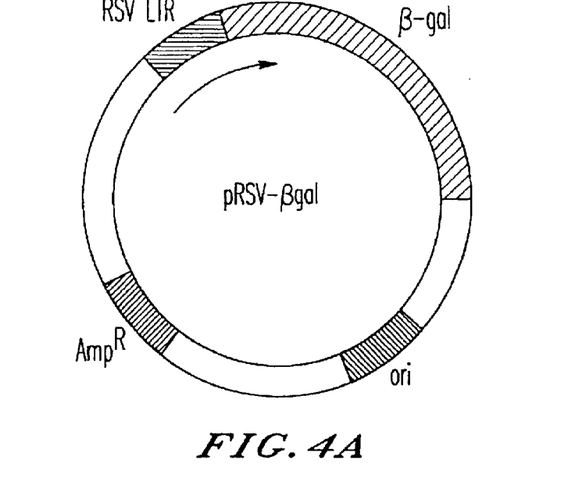
FIG. 4—Schematic method for introducing foreign genes into heart muscle cells.
Figure 4B:
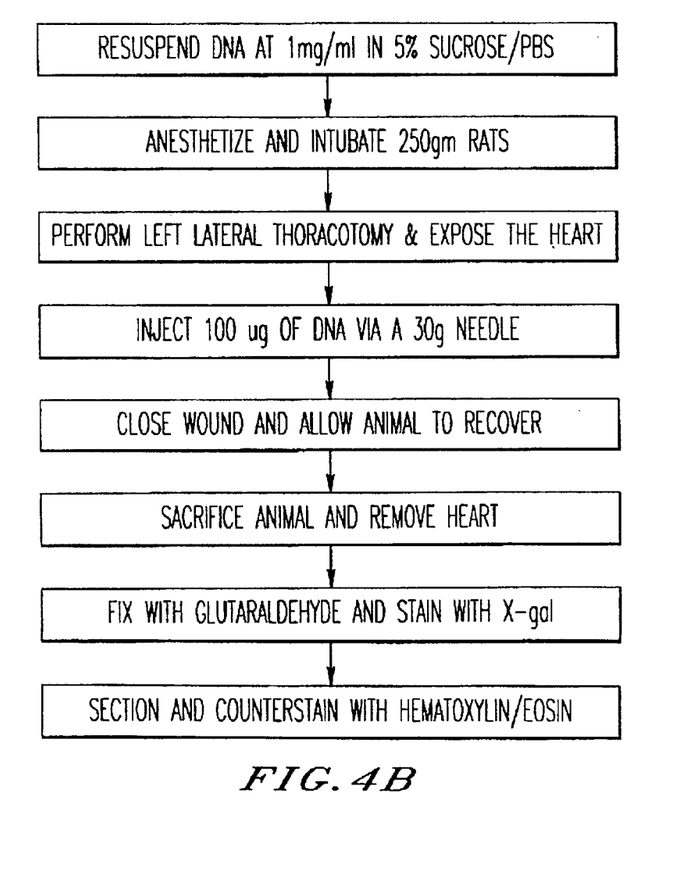
Figure 5A:
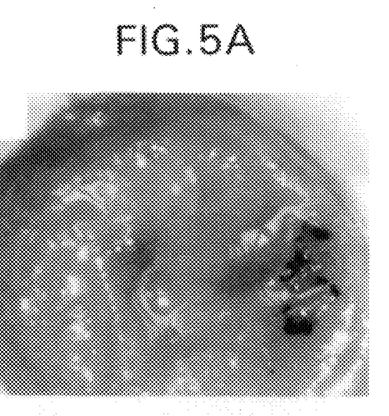
Figure 5B:
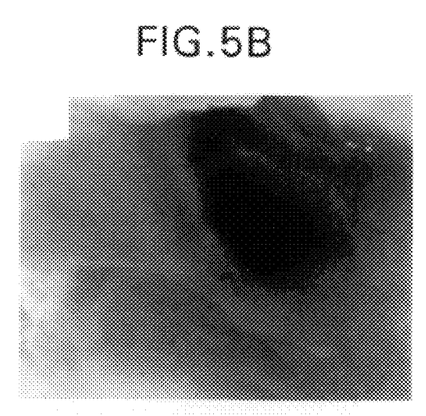
Figure 5C:
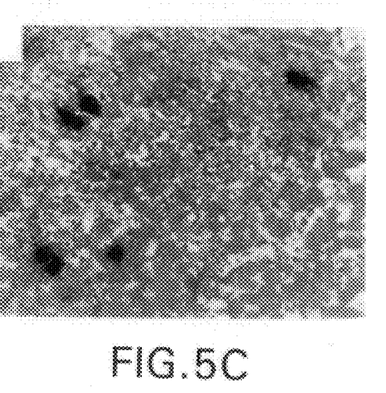
Figure 5D:
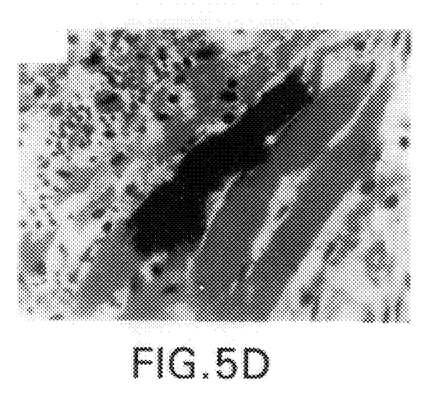
Figure 6:
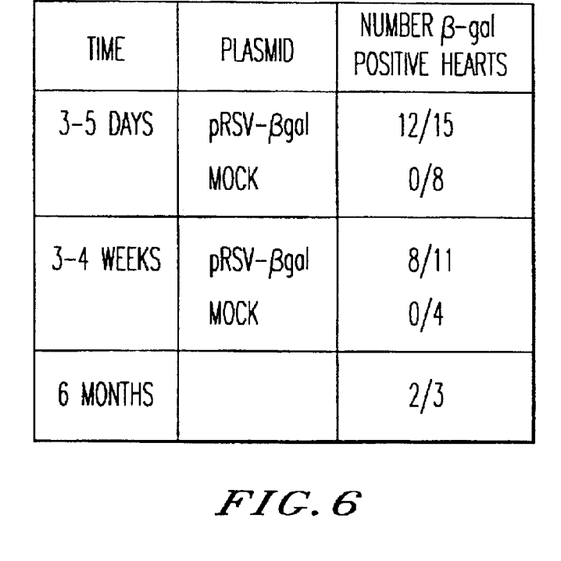
FIG. 6—Summary of cardiac injections with the β-gal expression vector.

The method that we have used for introducing foreign genes into heart muscle cells is shown schematically in FIG. 4. The method is most remarkable for its simplicity. A concentrated solution of genetic material (DNA) containing a single cloned gene is injected directly into the beating heart wall in normal six-week-old rats. The particular cloned gene that was used in all of our initial studies is a bacterial gene called β-galactosidase. We chose this gene because it is not normally expressed in heart cells. However, following injection of the DNA, we can detect its expression using a simple stain that turns cells that are expressing β-galactosidase blue. We were quite surprised to find that following injection into a normal rat heart, the β-galactosidase gene was taken up and expressed in heart muscle cells (FIG. 5). Thus, one can see areas of blue staining that correspond to the site of DNA injection and that represent upon high power magnification, expression of the β-galactosidase gene in cells that are easily identified as cardiac muscle by their striated pattern of appearance. It should be emphasized that the only cells that we have ever observed to take up and express the DNA are heart muscle cells. We have never observed expression in other cells in the heart such as fibroblasts or the cells lining the heart blood vessels. As shown in FIG. 6, more than 75% of the hearts receiving the injected DNA express the foreign gene, and this expression is stable for periods of at least six months.

Figure 7A:
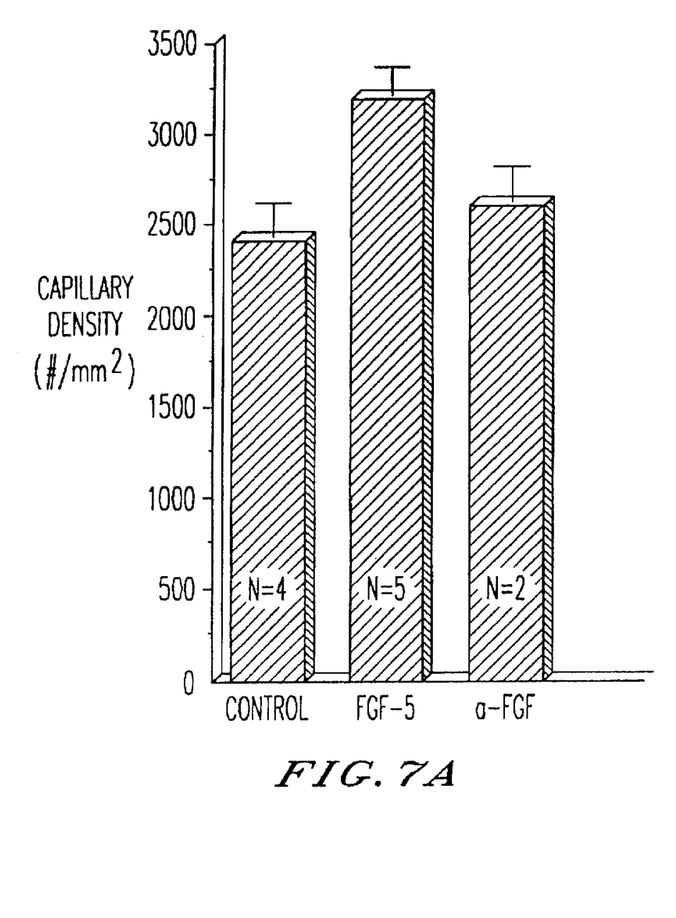
FIG. 7—Capillary growth after injection of heart wall with a fibroblast growth factor expression vector.
Figure 7B:
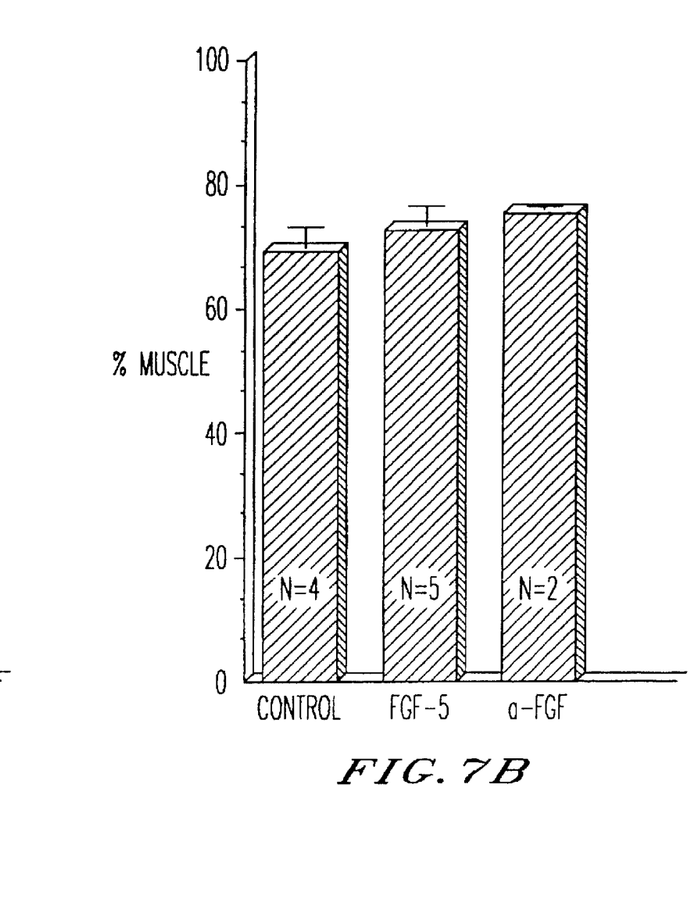

This method enables new blood vessel growth in areas of the heart that are currently not receiving sufficient blood or oxygen. Several million Americans are currently afflicted with atherosclerotic narrowings of the coronary arteries or blood vessels supplying the heart. In order to directly stimulate new blood vessel growth in areas of the heart that are not receiving sufficient blood because of coronary atherosclerosis, we have injected rat hearts with an angiogenesis factor gene, i.e. a gene called fibroblast growth factor (FGP-5), that stimulates new blood vessel growth. Following injection of FGF-5 DNA, we were able to show a 30–40% increase in the number of capillaries in the injected heart wall as compared to hearts injected with control DNA solutions (FIG. 7). Microscopic examination revealed that the structure of the capillaries in the injected hearts was normal, thus suggesting that these new capillaries can supply increased blood flow to the heart.

Rats have been injected with a plasmid-encoding human fibroblast growth factor-5 (hFGF-5) in an attempt to stimulate angiogenesis or collateral blood flow in the adult rat heart. Rats were sacrificed at 3 weeks following injection and capillary density was measured by computerized light microscopy. Rats injected with control vectors displayed approximately 2300 capillaries/mm$^2$ at the site of injection. In contrast, five animals injected with the FGF-5 expression vector displayed a 30–40% increase in capillary density with mean capillary densities of approximately 3400/mm$^2$ ($p<0.001$). Thus, direct injection of a fibroblast growth factor-5 expression vector stimulates collateral vessel formation in areas of injected myocardium.

In order to demonstrate recombinant gene expression in myocardium, a novel plasmid vector was constructed in which the bacterial β-galactosidase gene from the PMSV β-gal vector was cloned immediately downstream of the Rous sarcoma virus long terminal repeat (LTR). This vector was shown to produce high-level gene expression in rat neonatal cardiac myocytes following transfection in tissue culture. In order to introduce this plasmid into rat cardiac myocytes in vivo, 250 g Sprague-Dawley rats were anesthetized with pentobarbital plus ketamine, incubated, and ventilated with a Harvard respirator. A left lateral thoracotomy was performed to expose the beating heart and 100 mg of PRSV β-gal plasmid DNA in 100 ml of phosphate-buffered saline, plus 5% sucrose was injected into the apical portion of the beating left ventricle using a 30 gauge needle. Wounds were closed and animals were allowed to recover for three days to four weeks. Animals were sacrificed and hearts were removed, fixed with glutaraldehyde and stained with X-gal for detection of the β-galactosidase protein. In additional experiments, a plasmid vector in which the human fibroblast growth factor-5 cDNA is under the transcriptional control of the Rous sarcoma virus promoter has been constructed and injected into rat hearts using a similar technique.

It should be noted that the PRSV LTR used in these experiments is derived from a chicken virus. Previous studies have demonstrated that this element is very active in skeletal and cardiac muscle from a large number of species including human, mouse, and rat in vitro. Therefore, the results obtained with this expression vector in vivo in rats and mice should be directly applicable to humans since this element is transcriptionally active in human cells.

To increase transduction frequencies, similar injections into ischemic myocardium and injections with DC electrical countershock can be used. Additional vectors utilizing our recently-described cardiac Troponin C promoter/enhancer increase levels of recombinant gene expression.

Other features of the invention will become apparent in the course of the following examples which are given for illustration of the invention and are not intended to be limiting.

EXAMPLES

Cell Culture and Transient Transfections

Neonatal rat cardiac myocytes were isolated from 1–2-day-old Sprague-Dawley rats (Charles River Laboratories, Wilmington, Mass.) by collagenase digestion (Engelmann et al J. Mol Cell Cardiol. 1988; 20:169–77). This method results in the isolation of more than 90% cardiac myocytes.

Twenty-four hours after isolation, 1×10⁶ freshly isolated myocytes in a 60-mm collagen-coated dish (Collaborative Research Inc., Waltham, Mass.) were transfected with 15 μg of cesium chloride gradient-purified chloramphenicol acetyl transferase (CAT) reporter plasmid DNA plus 5 μg of pMSVβgal reference plasmid DNA as follows: 20 μg of plasmid DNA was resuspended in 1.5 ml of Opti-MEM (GIBCO, Grand Island, N.Y.) and added to 1.5 ml of Opti-MEM containing 50 μl of lipofectin reagent (BRL, Gaithersburg, Md.). The resulting mixture was added to one 60-mm plate of cardiac myocytes. After 5 hours at 37° C. in 5% $CO_2$, 3 ml of Medium 199 plus 5% fetal bovine serum (FCS) (GIBCO) was added to the cells, and the mixture was incubated at 37° C. for 48 hours. Cell extracts were prepared and normalized for protein content using a commercially available kit (Biorad, Richmond, Calif.). CAT and β-galactosidase assays were performed as previously described. Parmacek MS, Bengur A R, Vora A J, Leiden J M: J Biol Chem 1990 (in press).

Plasmids

Figure 8A:
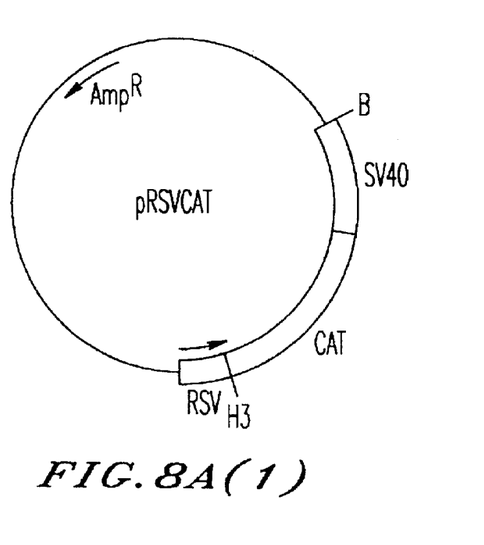
FIG. 8A—Schematic representation of pRSVCAT and pRSVgal.
Figure 8B:
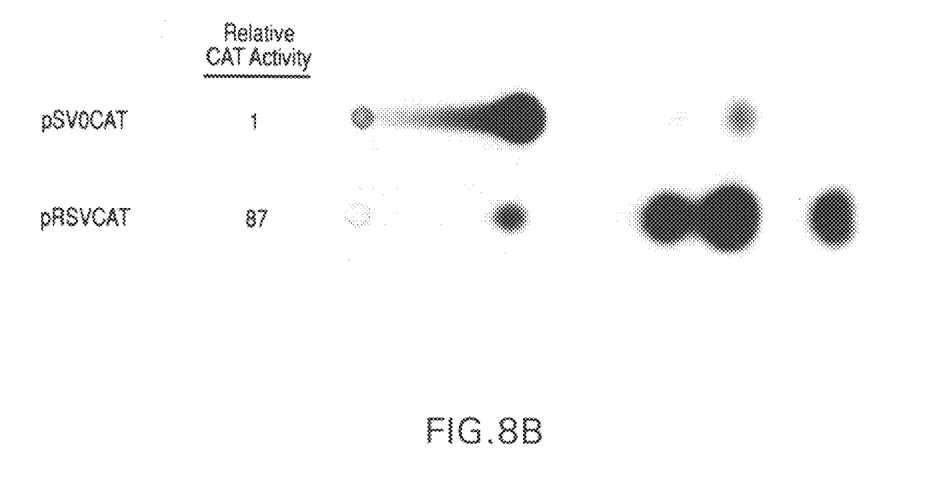
FIG. 8B—Transcriptional activity of the RSV LTR in rat neonatal cardiocytes in vitro.

The promoterless pSVOCAT plasmid (Gorman C M, Moffat L F, Howard B H: Recombinant genomes which express chloramphenicol acetyl-transferase in mammalian cells. Mol Cell Biol 1982;77:1432–1436) and the pRSVCAT (Gorman C, Padmanabhan R, Howard B H: High efficiency DNA-mediated transformation of primate cells. Science 1983;221:551–553) plasmid in which transcription of the bacterial CAT gene is under the control of the RSV promoter have been described previously. The pRSVβgal plasmid was constructed by cloning the 4.0-kb β-galactosidase gene from pMSVβgal (Donoghue M, Ernst H, Wentworth B, Nadal-Ginard B, Rosenthal N: A muscle-specific enhancer is located at the 3' end of the myosin light-chain ⅓ gene locus. Genes Dev 1988;2:1779–1790) into HindIII/BamHI-digested pRSVCAT (FIG. 8).

Injection of Recombinant DNA In Vivo

Six- to 11-week-old 250-g Sprague-Dawley rats were housed and cared for according to National Institutes of Health guidelines in the ULAM facility of the University of Michigan Medical Center. Rats were anesthetized with 20 mg/kg pentobarbitol i.p. and 60 mg/kg ketamine i.m., intubated, and ventilated with a Harvard (Harvard Apparatus, South Natick, Mass.) respirator. A left lateral thoracotomy was performed to expose the beating heart, and 100 μg of plasmid DNA in 100 μl of phosphate-buffered saline (PBS) containing 5% sucrose (PBS/sucrose) was injected into the apical portion of the beating left ventricle using a 30-g needle. Control animals were injected with 100 μl of PBS/sucrose alone. The animals were killed 3–5 or 21–30 days after injection by pentobarbitol euthanasia; hearts were removed via a median sternotomy, rinsed in ice-cold PBS, and processed for β-galactosidase activity.

Histochemical Analysis

Three-millimeter cross sections of the left ventricle were fixed for 5 minutes at room temperature with 1.25% glutaraldehyde in PBS, washed three times at room temperature in PBS, and stained for β-galactosidase activity with X-gal (Biorad) for 4–16 hours as described by Nabel et al. (Nabel E G, Plautz G, Boyce F M, Stanley J C, Nabel G J: Recombinant gene expression in vivo within endothelial cells of the arterial wall. Science 1989;244:1342–1344). The 3-mm sections were embedded with glycomethocyrlate, and 4–7 μm sections were cut and counterstained with hematoxylin and eosin as described previously. (Nabel E G, Plautz G, Boyce F M, Stanley J C, Nabel G J: Recombinant gene expression in vivo within endothelial cells of the arterial wall. Science 1989;244:1342–1344). Photomicroscopy was performed using Kodak Ektachrome 200 film and Leitz Laborlux D and Wild M8 microscopes. RSV LTR Promotes High-Level Gene Expression in Rat Neonatal Cardiocytes In Vitro To test the transcriptional activity of the RSV LTR in rodent cardiac myocytes, the pRSVCAT vector (Gorman C, Padmanabhan R, Howard B H: High efficiency DNA-mediated transformation of primate cells. Science 1983;221:551–553) in which expression of the bacterial CAT gene is under the control of the RSV LTR was transfected into primary neonatal rat cardiac myocytes using lipofectin. Two days after transfection, the cultures were harvested and assayed for CAT activity. All transfections also contained 5 μg of the pMSVβgal plasmid to correct for differences in transfection efficiencies. The RSV LTR was able to increase transcription of the CAT gene 87-fold compared with the-promoterless pSVOCAT control plasmid. The pRSVCAT-transfected cardiac myocyte extracts produced 95% acetylation in a standard thin-layer chromatography assay. By comparison, identically prepared extracts of 3T3 or HeLa cells transfected with this same vector produced 22% and 35% acetylation, respectively. Because the activities of cotransfected pMSVβgal reference plasmids were almost identical in all three transfections, these results demonstrated that the RSV LTR programs high-level transcription in primary cardiac myocytes in vitro.

The ability to unambiguously identify the cell types that are expressing recombinant gene products is an important requirement of all animal models of gene therapy. Because the bacterial β-galactosidase reporter gene (but not the bacterial CAT gene) allows direct histological visualization of recombinant gene expression, we constructed a pRSVβgal vector in which bacterial β-galactosidase gene expression is regulated by the RSV LTR promoter for further studies of recombinant gene expression in vivo (FIG. 11). Expression of β-Galactosidase Gene in Rat Cardiac Myocytes After Injection of pRSVβgal DNA into the Left Ventricular Wall In Vivo 100 μg of pRSVβgal DNA was resuspended in 100 μl of PBS containing 5% sucrose (PBS/sucrose) and injected via a 30-g needle directly into the beating left ventricular wall of 6–11-week-old Sprague-Dawley rat hearts. Control rats received injections of 100 βl of PBS/sucrose without DNA. Rats were killed either 3–5 days or 3–4 weeks after injection, and hearts were fixed and stained for β-galactosidase activity. β-Galactosidase activity as manifested by dark-blue staining was readily apparent to the naked eye in sections of three of four of the pRSVβgal-injected hearts at 3–5 days and four of the pRSVβgal-injected hearts and 3–4 weeks after DNA injections. This staining, which was focal and patchy, occurred only in a single area of each heart injected with pRSVβgal DNA and was not seen in five control hearts injected with PBS/saline alone. Failure to observe staining in two of nine of the pRSVβgal-injected hearts may have been due to the lack of DNA uptake or expression in these hearts or, more likely, to technical difficulties in successfully centering and anchoring the needle in the relatively thin beating left ventricular wall during the injection process.

Because the normal ventricular wall contains both myocytes and fibroblasts and because the injection of DNA might be expected to cause a localized inflammatory response, it was important to determine which cell types were expressing the recombinant β-galactosidase gene. Histochemical analysis of sections from hearts injected with the pRSVβgal DNA clearly demonstrated β-galactosidase activity within cardiac myocytes that were easily identified by their myofibrillar architecture. Between one and 10 positively staining myocytes were seen per high-power field, and these were often noncontiguous, suggesting that the uptake of DNA and/or its expression is a relatively low-frequency event. Because it was difficult to accurately identify the extent of DNA injection and because the positively staining area were quite focal and patchy, it was impossible to accurately quantitate either the percentage or the total number of cells expressing recombinant β-galactosidase activity in a given heart. However, it is clear that only a small fraction of cardiac myocytes expressed the recombinant protein. In addition, it is worth noting that sections from the 3–5 day postinjection hearts often showed evidence of an acute inflammatory response along the track of the needle and that in several cases fibrosis along the needle track was observed in sections from 3–4-week postinjection hearts.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method for inducing collateral blood vessel formation in a heart of a mammal, which comprises the steps of:
   a) injecting into heart muscle an expression vector comprising a DNA encoding a polypeptide that induces angiogenesis, and
   b) obtaining expression of said polypeptide in an amount sufficient to induce collateral blood vessel formation in said heart.

2. A method for improving abnormal cardiac function in a mammal, which comprises the steps of;
   a) injecting into heart muscle of said mammal a DNA encoding a polypeptide that induces angiogenesis, and
   b) obtaining expression of said polypeptide in said heart muscle in an amount that results in an increase blood flow within said heart muscle, thereby improving cardiac function.

3. A method for improving contractility of heart muscle in a mammal which comprises the steps of
   a) injecting into the heart muscle of said mammal a DNA encoding a polypeptide that induces angiogenesis, and
   b) obtaining expression of said polypeptide in an amount sufficient to increase blood flow within the heart muscle and to thereby improve heart muscle contractility.

4. The method of claims 1, 2 or 3, wherein said DNA is operably linked to a Rous sarcoma virus long terminal repeat.

5. The method of claims 1 or 2, wherein expression of the DNA encoding a polypeptide that induces angiogenesis improves muscle contractility.

6. The method of claims 1, 2 or 3, wherein said gene product is a fibroblast growth factor.

7. The method of claim 6, wherein said fibroblast gowth factor is FGF-5.

8. The method of claims 1, 2 or 3, wherein said polypeptide is secreted.

9. The method of claims 1, 2 or 3, wherein said gene product is injected directly into a ventricular wall of said heart.

10. The method of claims 1, 2 or 3, wherein said mammal is a human.

11. The method of claims 10, wherein said human suffers from atherosclerosis or myocardial ischemia.

12. The method of claim 10, wherein said human suffers from a myocardial disease.

13. The method of claim 12, wherein said myocardial disease is a cardiomyopathy or cardiac hypertrophy.

14. The method of claims 2 or 3, wherein said DNA comprises part of an expression vector.

15. The method of claim 14, wherein said expression vector is a non-infectious vector.

16. The method of claim 7, wherein said expression vector is a non-infectious vector.

* * * * *

UNITED STATES PATENT AND TRADEMARK OFFICE
CERTIFICATE OF CORRECTION

PATENT NO. : 6,316,419 B1
DATED : November 13, 2001
INVENTOR(S) : Jeffrey M. Leiden et al.

It is certified that error appears in the above-identified patent and that said Letters Patent is hereby corrected as shown below:

Title page,
Item [57], ABSTRACT,
Line 6, delete "Myocytes" and substitute -- myocytes -- in its place.

Column 11,
Line 33, delete "of;" and substitute -- of: -- in its place.

Column 12,
Line 37, delete "claim 7," and substitute -- claim 1, -- in its place.

Signed and Sealed this

Fifteenth Day of October, 2002

Attest:

JAMES E. ROGAN
Attesting Officer         Director of the United States Patent and Trademark Office